(12) United States Patent
Harrison et al.

(10) Patent No.: US 7,901,377 B1
(45) Date of Patent: Mar. 8, 2011

(54) INJECTION DEVICE

(75) Inventors: Nigel D. Harrison, Linton (GB);
Matthew J. Brady, Letchworth (GB);
David M. Johnston, Robbinsville, NJ
(US); Tim Barrow-Williams, St. Albans
(GB)

(73) Assignee: Cilag GmbH International, Zug (CH)

( * ) Notice: Subject to any disclaimer, the term of this patent is extended or adjusted under 35 U.S.C. 154(b) by 452 days.

(21) Appl. No.: 11/579,560

(22) PCT Filed: May 27, 2005

(86) PCT No.: PCT/GB2005/002117
§ 371 (c)(1),
(2), (4) Date: Oct. 3, 2008

(87) PCT Pub. No.: WO2005/115516
PCT Pub. Date: Dec. 8, 2005

(30) Foreign Application Priority Data

May 28, 2004 (GB) .................................. 0412056.4

(51) Int. Cl.
*A61M 5/20* (2006.01)
(52) U.S. Cl. ........................................ 604/156; 604/157
(58) Field of Classification Search .............. 604/68–72, 604/110, 156, 157, 192–198, 207–231
See application file for complete search history.

(56) References Cited

U.S. PATENT DOCUMENTS

| | | | |
|---|---|---|---|
| 4,394,863 A * | 7/1983 | Bartner | 604/90 |
| 5,026,349 A | 6/1991 | Schmitz et al. | |
| 5,137,516 A | 8/1992 | Rand et al. | |
| 5,176,643 A * | 1/1993 | Kramer et al. | 604/135 |
| 5,267,963 A | 12/1993 | Bachynsky | |
| 5,271,744 A | 12/1993 | Kramer et al. | |
| 5,295,965 A | 3/1994 | Wilmot | |
| 5,300,030 A | 4/1994 | Crossman et al. | |
| 5,405,362 A | 4/1995 | Kramer et al. | |
| 5,425,715 A | 6/1995 | Dalling et al. | |
| 5,451,210 A | 9/1995 | Kramer et al. | |
| 5,478,316 A | 12/1995 | Bitdinger et al. | |
| 5,487,732 A | 1/1996 | Jeffrey | |
| 5,567,160 A | 10/1996 | Massino | |
| 5,575,777 A | 11/1996 | Cover et al. | |
| 5,599,302 A | 2/1997 | Lilley et al. | |
| 5,599,309 A | 2/1997 | Marshall et al. | |
| 5,637,094 A * | 6/1997 | Stewart et al. | 604/135 |
| 5,681,291 A | 10/1997 | Galli | |
| 5,709,662 A | 1/1998 | Olive et al. | |
| 5,779,677 A | 7/1998 | Frezza | |
| 5,843,036 A | 12/1998 | Olive et al. | |
| 5,868,711 A | 2/1999 | Kramer et al. | |
| 5,879,327 A | 3/1999 | DeFarges et al. | |
| 5,913,843 A | 6/1999 | Jentzen | |
| 5,954,738 A | 9/1999 | LeVaughn et al. | |
| 5,957,897 A * | 9/1999 | Jeffrey | 604/223 |
| 5,960,797 A | 10/1999 | Kramer et al. | |

(Continued)

FOREIGN PATENT DOCUMENTS

EP 1124601 B1 12/2004

(Continued)

*Primary Examiner* — Nicholas D Lucchesi
*Assistant Examiner* — Gerald Landry, II
(74) *Attorney, Agent, or Firm* — Dean Garner

(57) ABSTRACT

An injection device (10; 110, 210) is described of the type that receives a syringe, extends it, discharges its contents and then retracts it automatically. The injection device makes use of a fluid-damped delay mechanism.

12 Claims, 4 Drawing Sheets

U.S. PATENT DOCUMENTS

| | | | |
|---|---|---|---|
| 6,015,438 A | 1/2000 | Shaw | |
| 6,045,534 A | 4/2000 | Jacobsen et al. | |
| 6,068,614 A | 5/2000 | Kimber et al. | |
| 6,077,247 A | 6/2000 | Marshall et al. | |
| 6,083,197 A | 7/2000 | Umbaugh | |
| 6,086,562 A | 7/2000 | Jacobsen et al. | |
| 6,090,078 A | 7/2000 | Erskine | |
| 6,090,897 A * | 7/2000 | Akasaki et al. | 428/520 |
| 6,099,503 A | 8/2000 | Stradella | |
| 6,099,504 A | 8/2000 | Gross | |
| 6,159,181 A | 12/2000 | Crossman et al. | |
| 6,179,812 B1 | 1/2001 | Botich et al. | |
| 6,186,980 B1 | 2/2001 | Brunel | |
| 6,203,530 B1 | 3/2001 | Stewart, Sr. | |
| 6,221,044 B1 | 4/2001 | Grecco | |
| 6,258,068 B1 | 7/2001 | Kirchhofer et al. | |
| 6,270,479 B1 | 8/2001 | Bergens et al. | |
| 6,280,421 B1 | 8/2001 | Kirchhofer et al. | |
| 6,371,939 B2 | 4/2002 | Bergens et al. | |
| 6,387,078 B1 | 5/2002 | Gillespie, III | |
| 6,391,003 B1 | 5/2002 | Lesch, Jr. | |
| 6,428,528 B2 | 8/2002 | Sadowski et al. | |
| 6,461,333 B1 | 10/2002 | Frezza | |
| 6,517,517 B1 | 2/2003 | Farrugia et al. | |
| 6,544,234 B1 | 4/2003 | Gabriel | |
| 6,565,540 B1 | 5/2003 | Perouse et al. | |
| 6,565,553 B2 | 5/2003 | Sadowski et al. | |
| 6,569,115 B1 | 5/2003 | Barker et al. | |
| 6,569,123 B2 | 5/2003 | Alchas et al. | |
| 6,569,124 B1 | 5/2003 | Perouse | |
| 6,572,581 B1 | 6/2003 | Landau | |
| 6,575,939 B1 | 6/2003 | Brunel | |
| 6,585,702 B1 | 7/2003 | Brunel | |
| 6,589,210 B1 | 7/2003 | Rolfe | |
| 6,595,957 B1 | 7/2003 | Griffiths et al. | |
| 6,595,962 B1 | 7/2003 | Perthu | |
| 6,607,508 B2 | 8/2003 | Knauer | |
| 6,607,510 B2 | 8/2003 | Landau | |
| 6,620,137 B2 | 9/2003 | Kirchhofer et al. | |
| 6,638,256 B2 | 10/2003 | Jansen et al. | |
| 6,641,554 B2 | 11/2003 | Landau | |
| 6,641,560 B1 | 11/2003 | Bechtold et al. | |
| 6,641,565 B1 | 11/2003 | Lavi et al. | |
| 6,645,170 B2 | 11/2003 | Landau | |
| 6,645,181 B1 | 11/2003 | Lavi et al. | |
| 6,656,163 B1 | 12/2003 | Marshall et al. | |
| 6,673,049 B2 | 1/2004 | Hommann et al. | |
| 6,676,630 B2 | 1/2004 | Landau et al. | |
| 6,689,093 B2 | 2/2004 | Landau | |
| 6,692,469 B1 | 2/2004 | Weekes et al. | |
| 6,699,220 B2 | 3/2004 | Rolfe | |
| 6,740,062 B2 | 5/2004 | Hjertman | |
| 6,743,199 B2 | 6/2004 | Shue et al. | |
| 6,743,203 B1 | 6/2004 | Pickhard et al. | |
| 6,746,429 B2 | 6/2004 | Sadowski et al. | |
| 6,767,336 B1 | 7/2004 | Kaplan | |
| 6,770,056 B2 | 8/2004 | Price et al. | |
| 6,776,777 B2 | 8/2004 | Barrelle | |
| 6,783,509 B1 | 8/2004 | Landau et al. | |
| 6,793,161 B1 | 9/2004 | Fujita et al. | |
| 6,796,967 B2 | 9/2004 | Jensen | |
| 6,811,548 B2 | 11/2004 | Jeffrey | |
| 6,846,303 B2 | 1/2005 | Eakins et al. | |
| 6,890,319 B1 | 5/2005 | Crocker | |
| 6,899,698 B2 | 5/2005 | Sams | |
| 6,932,793 B1 | 8/2005 | Marshall et al. | |
| 6,979,316 B1 | 12/2005 | Rubin et al. | |
| 7,066,907 B2 | 6/2006 | Crossman et al. | |
| 7,118,553 B2 | 10/2006 | Scherer | |
| 7,156,823 B2 | 1/2007 | Landau et al. | |
| 2001/0049496 A1 | 12/2001 | Kirchhofer et al. | |
| 2002/0072709 A1 | 6/2002 | Sadowski et al. | |
| 2002/0095120 A1 | 7/2002 | Larsen et al. | |
| 2003/0050609 A1 | 3/2003 | Sams | |
| 2003/0060773 A1 | 3/2003 | Nguyen | |
| 2003/0065286 A1 | 4/2003 | Landau | |
| 2003/0078546 A1 | 4/2003 | Jensen | |
| 2003/0088207 A1 | 5/2003 | Rogatchev et al. | |
| 2003/0093030 A1 | 5/2003 | Landau | |
| 2003/0093035 A1 | 5/2003 | Mohammed | |
| 2003/0105430 A1 | 6/2003 | Lavi et al. | |
| 2003/0109833 A1 | 6/2003 | Sahpe | |
| 2003/0135157 A1 | 7/2003 | Saulenas et al. | |
| 2003/0208164 A1 | 11/2003 | Botich et al. | |
| 2003/0212362 A1 | 11/2003 | Roser | |
| 2003/0212370 A1 | 11/2003 | Barrelle | |
| 2003/0212380 A1 | 11/2003 | Barrelle | |
| 2003/0225368 A1 | 12/2003 | Landau et al. | |
| 2003/0233070 A1 | 12/2003 | De La Serna et al. | |
| 2003/0236504 A1 | 12/2003 | Chen | |
| 2004/0015134 A1 | 1/2004 | Lavi et al. | |
| 2004/0039336 A1 | 2/2004 | Amark et al. | |
| 2004/0039366 A1 | 2/2004 | MacLeod | |
| 2004/0069044 A1 | 4/2004 | Lavi et al. | |
| 2004/0087897 A1 | 5/2004 | Hjertman | |
| 2004/0111054 A1 | 6/2004 | Landau et al. | |
| 2004/0111057 A1 | 6/2004 | Wilkinson | |
| 2004/0133159 A1 | 7/2004 | Haider et al. | |
| 2004/0138618 A1 | 7/2004 | Mazzoni | |
| 2004/0143224 A1 | 7/2004 | Field et al. | |
| 2004/0153033 A1 | 8/2004 | Mazzoni | |
| 2005/0011780 A1 | 1/2005 | Simon et al. | |
| 2005/0020979 A1 | 1/2005 | Westbye et al. | |
| 2005/0027255 A1 | 2/2005 | Lavi et al. | |
| 2005/0033234 A1 | 2/2005 | Sadowski et al. | |
| 2005/0035029 A1 | 2/2005 | Grob | |
| 2005/0040716 A1 | 2/2005 | Schmid et al. | |
| 2005/0049550 A1 | 3/2005 | Kirchhofer et al. | |
| 2005/0049561 A1 | 3/2005 | Hommann et al. | |
| 2005/0075608 A1 | 4/2005 | Holdgate et al. | |
| 2005/0085776 A1 | 4/2005 | Hommann et al. | |
| 2005/0090782 A1 | 4/2005 | Marshall et al. | |
| 2005/0097238 A1 | 5/2005 | Oomori et al. | |
| 2005/0101919 A1 | 5/2005 | Brunnberg | |
| 2005/0124940 A1 * | 6/2005 | Martin et al. | 604/209 |
| 2005/0125019 A1 | 6/2005 | Kudrna et al. | |
| 2005/0203466 A1 | 9/2005 | Hommann et al. | |
| 2005/0215951 A1 | 9/2005 | Saulenas et al. | |
| 2005/0222539 A1 | 10/2005 | Gonzales et al. | |
| 2005/0261634 A1 | 11/2005 | Karlsson | |
| 2005/0273054 A1 | 12/2005 | Asch | |
| 2005/0273055 A1 * | 12/2005 | Harrison et al. | 604/136 |
| 2005/0277885 A1 | 12/2005 | Scherer | |
| 2005/0277886 A1 | 12/2005 | Hommann et al. | |
| 2005/0288633 A1 | 12/2005 | Jeffrey | |
| 2006/0069345 A1 | 3/2006 | Anderson et al. | |
| 2006/0161111 A1 | 7/2006 | Potter et al. | |
| 2006/0224124 A1 | 10/2006 | Scherer | |
| 2006/0258990 A1 | 11/2006 | Weber | |
| 2006/0270986 A1 | 11/2006 | Hommann et al. | |
| 2007/0027430 A1 | 2/2007 | Hommann | |
| 2007/0078382 A1 | 4/2007 | Hommann et al. | |
| 2007/0142787 A1 | 6/2007 | Scherer | |

FOREIGN PATENT DOCUMENTS

| | | |
|---|---|---|
| WO | WO 88/10129 A1 | 12/1988 |
| WO | WO 93/23098 A1 | 11/1993 |
| WO | WO 94/04207 A1 | 3/1994 |
| WO | WO 95/29720 A1 | 11/1995 |
| WO | WO 95/35126 A1 | 11/1995 |
| WO | WO 97/13538 A1 | 4/1997 |
| WO | WO 99/22789 A1 | 5/1999 |
| WO | WO 99/59658 A1 | 11/1999 |
| WO | WO 00/64515 A1 | 11/2000 |
| WO | WO 03/039633 A2 | 5/2003 |
| WO | WO 03/051434 A2 | 6/2003 |
| WO | WO 03/092771 | 11/2003 |
| WO | WO 03/097133 | 11/2003 |
| WO | WO 2004/035117 A2 | 4/2004 |
| WO | WO 2004/047891 A1 | 6/2004 |
| WO | WO 2005/082438 A1 | 9/2005 |
| WO | WO 2005/097238 A3 | 10/2005 |

* cited by examiner

INJECTION DEVICE

BACKGROUND TECHNOLOGY

The present invention relates to an injection device of the type that receives a syringe, extends it, discharges its contents and then retracts it automatically. Devices of this general description are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring.

However, problems have arisen in devices such as these that make it difficult to ensure both complete discharge of the syringe contents and reliable release of the syringe from the drive spring. Because of the stack up of tolerances of the various components of the device, a certain margin of safety must be built into the activation of the release mechanism, to ensure that it is effective. The consequence of underestimating the safety margin is that the release mechanism may fail to operate even once the syringe contents have been discharged, which is unsatisfactory in a device that is supposed to retract automatically, particularly for self-administered drugs. On the other hand, overestimating the safety margin may mean that some of the syringe contents are discharged after the syringe has retracted, which results firstly in a short dose and secondly in what may be termed a "wet" injection. Wet injections are undesirable for the squeamish, particularly in connection with self-administered drugs.

UK patent applications nos. 0210123, 0229384 and 0325596 describe a series of injection devices designed to deal with this problem. Each makes use of a neat trick that delays the release of the syringe for a certain period of time after the release mechanism has been activated, in an attempt to ensure that the syringe has been completely discharged. The devices illustrated in UK patent applications no. 0325596 make use of a fluid-damped delay mechanism that is particularly effective in ensuring complete discharge of the syringe contents, but creates problems of its own. Firstly, the use of a fluid-damped delay mechanism requires the creation of a fluid-tight reservoir. Thus, the manufacturing tolerances of those components that define the fluid reservoir must be fine, or seals must be used to prevent the fluid from leaking out before its job is done. Secondly, it is undesirable for the fluid to leak out of its reservoir even when the device has been actuated, because that could give rise to a simulated wet injection, or to the impression that the syringe contents may have leaked within the device. Neither is conducive to the peace-of-mind of self-administered drug users. Again, fine tolerances or seals are called for, which pushes up the price of manufacture. For injection devices that are designed to be disposable, as many will be, every penny counts.

SUMMARY OF THE INVENTION

The injection devices of the present invention make use of a fluid-damped delay mechanism, but suffer from none of the disadvantages just described, as will now be explained.

An injection device according to a first aspect of the present invention comprises:

- a housing adapted to receive a syringe having a discharge nozzle, the housing including means for biasing the syringe from an extended position in which the discharge nozzle extends from the housing to a retracted position in which the discharge nozzle is contained within the housing;
- an actuator;
- a drive acted upon by the actuator and in turn acting on the syringe to advance it from its retracted position to its extended position and discharge its contents through the discharge nozzle;
- a decoupling mechanism, activated when the drive has been advanced to a nominal decoupling position, to decouple a first component of the device from a second component, whereupon the first component of the device moves relative to the second component;
- a release mechanism, activated when the first component has reached a nominal release position relative to the second, to release the syringe from the action of the actuator, whereupon the biasing means restores the syringe to its retracted position; and
- a highly viscous fluid damping the movement of the first component relative to the second, so that the release of the syringe is delayed after the activation of the decoupling mechanism to allow the remaining contents of the syringe to be discharged before the syringe is released.

The delay between the activation of the decoupling mechanism and the activation of the release mechanism is used to compensate for any stacking of tolerances. Although triggering of the decoupling mechanism can be designed to occur before the contents of the syringe are fully discharged, the delay is so chosen that, for all variations within the intended tolerances of the components, release of the syringe will not occur until after its contents have been fully discharged. It thus becomes possible to ensure that the syringe contents have been discharged before it is retracted, without having to comply with unrealistically fine tolerances.

By "highly viscous fluid" is here meant a fluid that, at 25° C., has a dynamic viscosity of 3000 centiPoise or more. Methods are known in the art for determining the dynamic viscosity of both Newtonian fluids, which are preferred in this invention, and non-Newtonian fluids. A preferred method, which is applicable to both Newtonian and non-Newtonian fluids is described in the Annex to this application. This method derives an average value for dynamic viscosity at shear rates that are determined by the test apparatus and the fluid under test and are reproducible.

Greater improvements can be obtained with fluids that, at 25° C., have a dynamic viscosity of 6000 centiPoise or more and, better still, 12000 centiPoise or more. The preferred fluid is DOW CORNING 111 Silicone Compound valve lubricant and sealant which, at 25° C., has a dynamic viscosity of about 12500 centiPoise.

Because a highly viscous fluid is, by definition, highly resistant to flow, certain constraints are avoided. Firstly, it is no longer necessary to create a completely fluid-tight reservoir, because imperfections in the reservoir boundaries will not provide an escape route for a that does not flow under the prevailing conditions. Thus, the manufacturing tolerances of those components that define fluid reservoir need not be fine and nor need seals be used. Secondly, simulated wet injections and the impression that the syringe contents may have leaked within the device are problems no longer, since the highly viscous fluid will not flow to a sufficient extent to give rise to these misapprehensions.

To reduce the component count and ensure the injection device remains compact, the first and second components of the device may be constituted by first and second elements of the drive, of which the first is acted upon by the actuator and the second acts upon the syringe, the first drive element being capable of movement relative to the second when the former is acted upon by the actuator and the latter is restrained by the syringe. As will be recognised, the relative movement of the first and second drive elements that is damped by the highly viscous fluid, is driven by the actuator. Use of the actuator in this way keeps down the component count.

A reservoir for the highly viscous fluid may be defined in part by the first drive element and in part by the second drive element, the volume of the reservoir tending to decrease as the first drive element moves relative to the second when acted upon by the actuator, the reservoir containing the highly viscous fluid and having a vent through which the fluid escapes as the volume of the reservoir decreases. This probably provides the simplest and most compact realisation of the fluid damping mechanism using a highly viscous fluid.

An injection device according to a second aspect of the present invention comprises:

- a housing adapted to receive a syringe having a discharge nozzle, the housing including means for biasing the syringe from an extended position in which the discharge nozzle extends from the housing to a retracted position in which the discharge nozzle is contained within the housing;
- an actuator;
- first and second drive elements, of which the first is acted upon by the actuator and the second acts upon the syringe to advance it from its retracted position to its extended position and discharge its contents through the discharge nozzle, the first drive element being capable of movement relative to the second when the former is acted upon by the actuator and the latter is restrained by the syringe;
- a reservoir defined in part by the first drive element and in part by the second drive element, the volume of the reservoir tending to decrease as the first drive element moves relative to the second when acted upon by the actuator, the reservoir containing a highly viscous fluid and having a vent through which the fluid escapes as the volume of the reservoir decreases; and
- a release mechanism, activated when the first drive element has been advanced to a nominal release position, and adapted to release the syringe from the action of the actuator, whereupon the biasing means restores the syringe to its retracted position.

In this aspect of the invention, account is taken of the fact that, where the highly viscous fluid damps relative movement of two elements of the drive, the decoupling of the two drive elements need not be accomplished by a decoupling mechanism. Other possibilities exist, including the use of two components that include a frangible coupling or no coupling other than that provided by static friction between the two components. Nonetheless, a delay between the decoupling of the drive elements and the activation of the release mechanism is present, and is used as described above.

Thus, the injection device may further comprise a coupling that prevents the first drive element from moving relative to the second until they have been advanced to a nominal decoupling position that is less advanced than the said nominal release position. The coupling may, and preferably does, comprises a decoupling mechanism, activated when the drive elements have been advanced to the said nominal decoupling position.

Two forms of coupling and decoupling mechanisms are specifically proposed, although it is acknowledged that other possibilities exist. In its first form, the coupling is a third drive element acting upon the first and second drive elements. In this case, the decoupling mechanism is adapted to decouple the third drive element from the second so that the third drive element acts only it no longer once the said nominal decoupling position has been reached, thus allowing the first drive element to move relative to the second, and the release mechanism is adapted to decouple the third drive element from the first so that the third drive element acts upon it no longer once the said nominal release position has been reached, thus releasing the syringe from the action of the actuator.

In its second form, the coupling comprises cooperating features of the first and second drive elements allowing the first to act upon the second. In this case, the decoupling mechanism is adapted to decouple the first drive element from the second so that the first drive element acts no longer on the second once the said nominal decoupling position has been reached, thus allowing the first drive element to move relative to the second, and the release mechanism is adapted to decouple the first drive element from the actuator so that the actuator acts upon it no longer once the said nominal release position has been reached, thus releasing the syringe from the action of the actuator.

In general, for simplicity of manufacture of the component parts by injection moulding, one drive element may include a stem and the other a bore that is open at one end to receive the stem, the bore and the stem thus defining the fluid reservoir.

To reduce further the possibility of simulated wet injections or the impression that the syringe contents may have leaked within the device, the vent may be in communication with a collection chamber defined by one drive element, within which the escaped fluid is collected. In this case, for simplicity of manufacture, it is preferred that one drive element include a stem and define the vent and the collection chamber and the other drive element include a blind bore that is open at one end to receive the stem and closed at the other, the bore and the stem thus defining the fluid reservoir. Again, for greater simplicity of manufacture by injection moulding, the collection chamber may be defined by a bore in the said one element, being open at one end and closed at the other but for the vent.

BRIEF DESCRIPTION OF THE DRAWINGS

The invention will now be described by way of example with reference to the accompanying drawings, in which.

DETAILED DESCRIPTION

Figure 1:
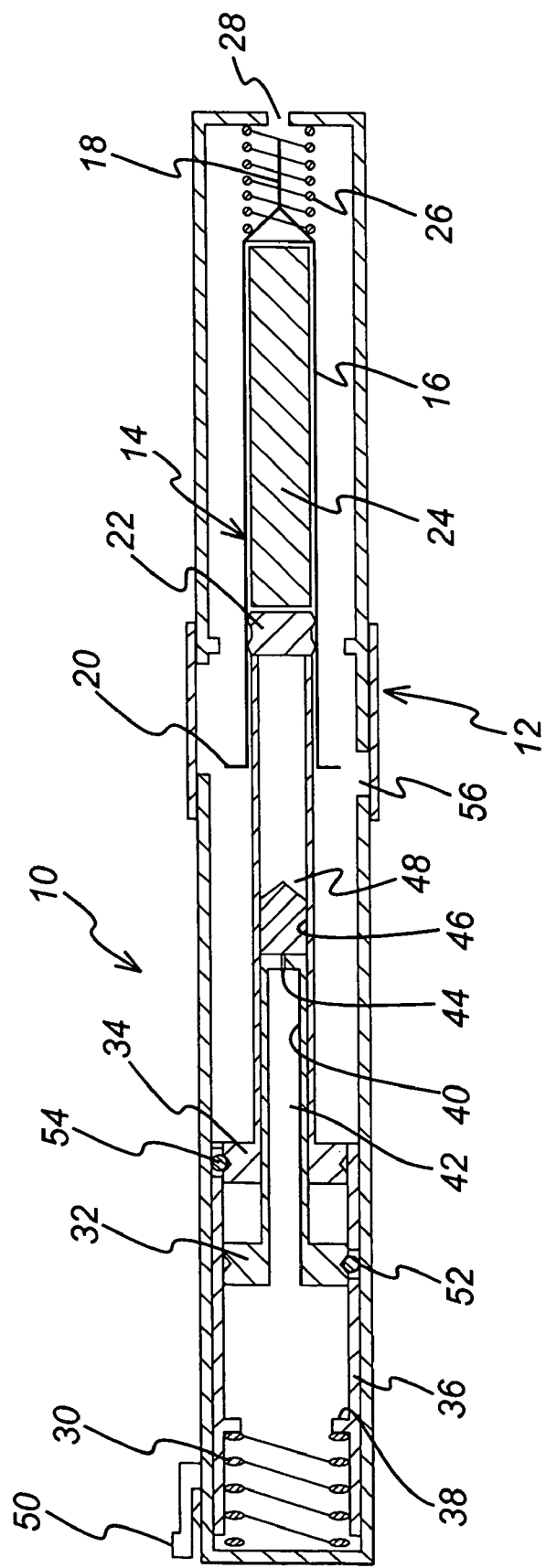
FIG. 1 is a schematic illustration of a first embodiment.

FIG. 1 shows an injection device 10 in which a housing 12 contains a hypodermic syringe 14. The syringe 14 is of conventional type, including a syringe body 16 terminating at one end in a hypodermic needle 18 and at the other in a flange 20, and a rubber bung 22 that constrains a drug 24 to be administered within the syringe body 16. The conventional plunger that would normally be connected to the bung 22 and used to discharge the contents of the syringe 14 manually has been removed and replaced with a drive element as will be described below. Whilst the syringe illustrated is of hypodermic type, this need not necessarily be so. Transcutaneous or ballistic dermal and subcutaneous syringes may also be used with the injection device of the present invention. Generally, the syringe must include a discharge nozzle, which in a hypodermic syringe is the needle 18. As illustrated, the housing includes a return spring 26 that biases the syringe 14 from an extended position in which the needle 18 extends from an aperture 28 in the housing 12 to a retracted position in which the discharge nozzle 18 is contained within the housing 12.

At the other end of the housing is an actuator, which here takes the form of a compression drive spring 30. Drive from the drive spring 30 is transmitted via a multi-component drive to the syringe 14 to advance it from its retracted position to its extended position and discharge its contents through the needle 18. The drive accomplishes this task by acting on the bung 22. Static friction between the bung 22 and the syringe body 16 initially ensures that bung 22 and body 16 advance together, until the return spring 26 bottoms out or the syringe body 16 meets some other obstruction (not shown) that retards its motion.

The multi-component drive between the drive spring 30 and the syringe 14 consists of three principal components. A first drive element 32 and a second drive element 34 are each acted upon by a third drive element 36, in internal shoulder 38 of which is acted upon by the drive spring 30. Thus, the drive spring 30 causes the third drive element 36 to move, which in turn causes the first and second drive elements 32, 34 to move in tandem. The third drive element 36 is coupled to the first and second drive elements 32, 34 by means of respective ball latches 52, 54, of which more later.

The first drive element 32 includes a hollow stem 40, the inner cavity of which forms a collection chamber 42 in communication with a vent 44 that extends from the collection chamber through the end of the stem 40. The second drive element 34 includes a blind bore 46 that is open at one end to receive the stem 40 and closed at the other. As can be seen, the bore 46 and the stem 40 defining a fluid reservoir 48, within which a highly viscous fluid is contained.

A trigger 50 is provided at the end of the housing 12 remote from the exit aperture 28 for the hypodermic needle 18. The trigger, when operated, serves to decouple the third drive component 36 from the housing 12, allowing it to move relative to the housing 12 under the influence of the drive spring 30. The operation of the device is then as follows.

Initially, the drive spring 30 moves the third drive element 36 and the third drive element 36 moves the first and second drive elements 32, 34 by acting through the ball latches 52, 54. The second drive element 34 moves the rubber bung 22, which by virtue of static friction and hydrostatic forces acting through the drug 24 to be administered moves the syringe body 16 against the action of the return spring 26. The return spring 26 compresses and the hypodermic needle 18 emerges from the exit aperture 28 of the housing 12. This continues until the return spring 26 bottoms out or the syringe body 16 meets some other obstruction (not shown) that retards its motion. Because the static friction between the bung 22 and the syringe body 16 and the hydrostatic forces acting through the drug 24 to be administered are not sufficient to resist the full drive force developed by the drive spring 30, at this point the bung 22 begins to move within the syringe body 16 and the drug 24 begins to be discharged. Dynamic friction between the bung 22 and the syringe body and hydrostatic and hydrodynamic forces now acting through the drug 24 to be administered are, however, sufficient to retain the return spring 26 in its compressed state, so the hypodermic needle 18 remains extended.

Before the bung 22 reaches the end of its travel within the syringe body 16, so before the contents of the syringe have fully discharged, the ball latch 54 linking the third drive element 36 with the second drive element 34 reaches a region 56 of the housing 12 at which the inner diameter of the housing 12 is enlarged. The balls in the ball latch 54 move laterally outwards from the position shown to a position at which they no longer couple the third drive element 36 to the second drive element 34, aided by the bevelled surfaces on the second drive element 34, fast against which they are normally retained by the inner surface of the housing 12. Once this happens, the third drive element 36 acts no longer on the second drive element 34, allowing the first and third drive elements 32, 36 to move relative to the second drive element 34.

Because the highly viscous fluid is contained within a reservoir 48 defined between the end of the first drive element 32 and the blind bore 46 in the second drive element 34, the volume of the reservoir 46 will tend to decrease as the first drive element 32 moves relative to the second drive element 34 when the former is acted upon by the drive spring 30. As the reservoir 48 collapses, highly viscous fluid is forced through the vent 44 into the collection chamber 42. Thus, once the ball latch 54 has been released, some of the force exerted by the drive spring does work on the highly viscous fluid, causing it to flow though the constriction formed by the vent 44; the remainder acts hydrostatically through the fluid and through friction between the first and second drive elements 32, 34, thence via the second drive element 34 and onto the bung 22. Losses associated with the flow of the highly viscous fluid do not attenuate the force acting on the body of the syringe to a great extent. Thus, the return spring 26 remains compressed and the hypodermic needle remains extended.

It has been found that with a highly viscous fluid possessing a dynamic viscosity of 12,000 centistokes or more, the vent 44 may consist of a circular aperture 0.7 mm in diameter. This is a relatively large diameter and is easy to form using conventional injection moulding techniques. Thinner fluids require smaller holes and thicker ones require larger holes. Forcing such a fluid through such a vent 44 is effective to damp the movement of the first and second drive elements 32, 34 relative to each other. Moreover, such a fluid resists flow to such an extent that it will not, under its own weight, flow from the open end of the collection chamber 42. Thus, the collection chamber 42 need not be closed at the end remote from the vent 44, making the first drive element 32 easy to manufacture by injection moulding.

After a time, the bung 22 completes its travel within the syringe body 16 and can go no further. At this point, the contents of the syringe 14 are completely discharged and the force exerted by the drive spring 30 acts to retain the bung 22 in its terminal position and to continue to cause the highly viscous fluid to flow though the vent, allowing the first drive element 32 to continue its movement.

Before the reservoir 48 of fluid is exhausted, the ball latch 52 linking the third drive element 36 with the first drive element 32 reaches the region 56 of the housing 12 at which the inner diameter of the housing 12 is enlarged. The balls in the ball latch 52 move laterally outwards from the position shown to a position at which they no longer couple the third drive element 36 to the first drive element 32, aided by the bevelled surfaces on the first drive element 32, fast against which they are normally retained by the inner surface of the housing 12. Once this happens, the third drive element 36 acts no longer on the first drive element 32, allowing the first and third drive elements 32, 36 to move relative each other. At this point, of course, the syringe 14 is released, because the forces developed by the drive spring 30 are no longer being transmitted to the syringe 14, and the only force acting on the syringe will be the return force from the return spring 26. Thus, the syringe 14 is now returned to its retracted position and the injection cycle is complete.

Figure 2:
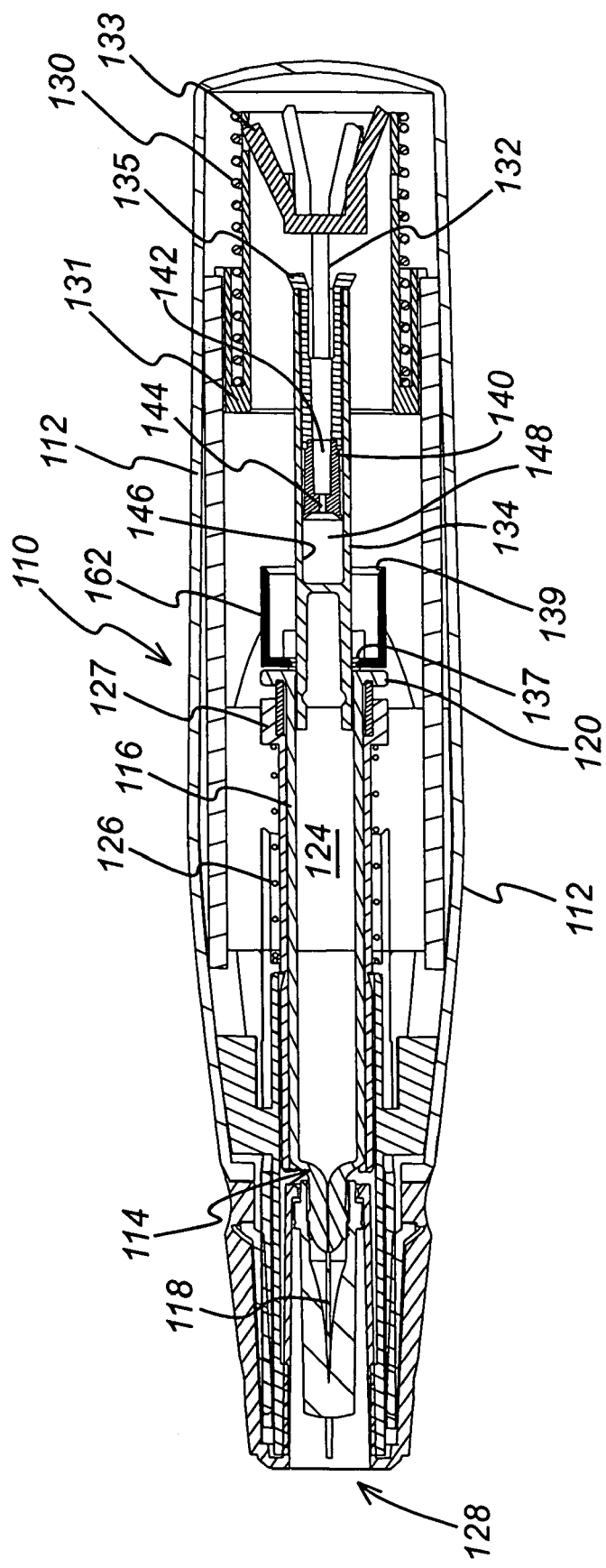
FIG. 2 is a second.

FIG. 2 shows another injection device 110 in which a housing 112 contains a hypodermic syringe 114. The syringe 114 is again of conventional type, including a syringe body 116 terminating at one end in a hypodermic needle 118 and at the other in a flange 120. The conventional plunger that would normally be used to discharge the contents of the syringe 114 manually have been removed and replaced with a drive element 134 as will be described below, which terminates in a bung 122. The bung 122 constrains a drug 124 to be administered within the syringe body 116. Whilst the syringe illustrated is of hypodermic type, this need not necessarily be so. As illustrated, the housing includes a return spring 126 that biases the syringe 114 from an extended position in which the needle 118 extends from an aperture 128 in the housing 112 to a retracted position in which the discharge nozzle 118 is contained within the housing 112. The return spring 126 acts on the syringe 114 via a sleeve 127.

At the other end of the housing is an actuator, which here takes the form of a compression drive spring 130. Drive from the drive spring 130 is transmitted via a multi-component drive to the syringe 114 to advance it from its retracted position to its extended position and discharge its contents through the needle 118. The drive accomplishes this task by acting directly on the drug 124 and the syringe 114. Hydrostatic forces acting through the drug and, to a lesser extent, static friction between the bung 122 and the syringe body 116 initially ensure that they advance together, until the return spring 126 bottoms out or the syringe body 116 meets some other obstruction that retards its motion.

The multi-component drive between the drive spring 130 and the syringe 114 consists of three principal components. A drive sleeve 131 takes drive from the drive spring 130 and transmits it to flexible latch arms 133 on a first drive element 132. This in turn transmits drive via flexible latch arms 135 to a second drive element, the drive element 134 already mentioned.

The first drive element 132 includes a hollow stem 140, the inner cavity of which forms a collection chamber 142 in communication with a vent 144 that extends from the collection chamber through the end of the stem 140. The second drive element 134 includes a blind bore 146 that is open at one end to receive the stem 140 and closed at the other. As can be seen, the bore 146 and the stem 140 define a fluid reservoir 148, within which a highly viscous fluid is contained.

A trigger (not shown) is provided in the middle of the housing 112. The trigger, when operated, serves to decouple the drive sleeve 131 from the housing 112, allowing it to move relative to the housing 112 under the influence of the drive spring 130. The operation of the device is then as follows.

Initially, the drive spring 130 moves the drive sleeve 131, the drive sleeve 131 moves the first drive element 32 and the first drive element 132 moves the second drive element 134, in each case by acting through the flexible latch arms 133, 135. The second drive element 134 moves and, by virtue of static friction and hydrostatic forces acting through the drug 124 to be administered, moves the syringe body 116 against the action of the return spring 126. The return spring 126 compresses and the hypodermic needle 118 emerges from the exit aperture 128 of the housing 112. This continues until the return spring 126 bottoms out or the syringe body 116 meets some other obstruction that retards its motion. Because the static friction between the second drive element 134 and the syringe body 116 and the hydrostatic forces acting through the drug 124 to be administered are not sufficient to resist the full drive force developed by the drive spring 130, at this point the second drive element 134 begins to move within the syringe body 116 and the drug 124 begins to be discharged. Dynamic friction between the second drive element 134 and the syringe body 116 and hydrostatic forces acting through the drug 124 to be administered are, however, sufficient to retain the return spring 126 in its compressed state, so the hypodermic needle 118 remains extended.

Before the second drive element 134 reaches the end of its travel within the syringe body 116, so before the contents of the syringe have fully discharged, the flexible latch arms 135 linking the first and second drive elements 132, 134 reach a constriction 137 within the housing 112. The constriction 137 moves the flexible latch arms 135 inwards from the position shown to a position at which they no longer couple the first drive element 136 to the second drive element 134, aided by the bevelled surfaces on the constriction 137. Once this happens, the first drive element 136 acts no longer on the second drive element 134, allowing the first drive element 132 to move relative to the second drive element 134.

Because the highly viscous fluid is contained within a reservoir 148 defined between the end of the first drive element 132 and the blind bore 146 in the second drive element 134, the volume of the reservoir 146 will tend to decrease as the first drive element 132 moves relative to the second drive element 134 when the former is acted upon by the drive spring 130. As the reservoir 148 collapses, highly viscous fluid is forced through the vent 144 into the collection chamber 142. Thus, once the flexible latch arms 135 have been released, the force exerted by the drive spring 130 does work on the highly viscous fluid, causing it to flow though the constriction formed by the vent 144, and acts hydrostatically through the fluid and through friction between the first and second drive elements 132, 134, thence via the second drive element 134. Losses associated with the flow of the highly viscous fluid do not attenuate the force acting on the body of the syringe to a great extent. Thus, the return spring 126 remains compressed and the hypodermic needle remains extended.

After a time, the second drive element 134 completes its travel within the syringe body 116 and can go no further. At this point, the contents of the syringe 114 are completely discharged and the force exerted by the drive spring 130 acts to retain the second drive element 134 in its terminal position and to continue to cause the highly viscous fluid to flow though the vent 144, allowing the first drive element 132 to continue its movement.

Before the reservoir 148 of fluid is exhausted, the flexible latch arms 133 linking the drive sleeve 131 with the first drive element 132 reach another constriction 139 within the housing 112. The constriction 139 moves the flexible latch arms 133 inwards from the position shown to a position at which they no longer couple the drive sleeve 131 to the first drive element 132, aided by the bevelled surfaces on the constriction 139. Once this happens, the drive sleeve 131 acts no longer on the first drive element 132, allowing them to move relative each other. At this point, of course, the syringe 114 is released, because the forces developed by the drive spring 130 are no longer being transmitted to the syringe 114, and the only force acting on the syringe will be the return force from the return spring 126. Thus, the syringe 114 is now returned to its retracted position and the injection cycle is complete.

All this takes place, of course, only once the cap 111 has been removed from the end of the housing 112. As can be seen from FIG. 3, the end of the syringe is sealed with a boot 123. The central boss 121 of the cap that fits within the sleeve 119 when the cap 111 is installed on the housing 112, is hollow at the end and the lip 125 of the hollow end is bevelled on its leading edge 157, but not its trailing edge. Thus, as the cap 111 is installed, the leading edge 157 of the lip 125 rides over a shoulder 159 on the boot 123. However, as the cap 111 is removed, the trailing edge of the lip 125 will not ride over the shoulder 159, which means that the boot 123 is pulled off the syringe 114 as the cap 111 is removed.

Figure 3:
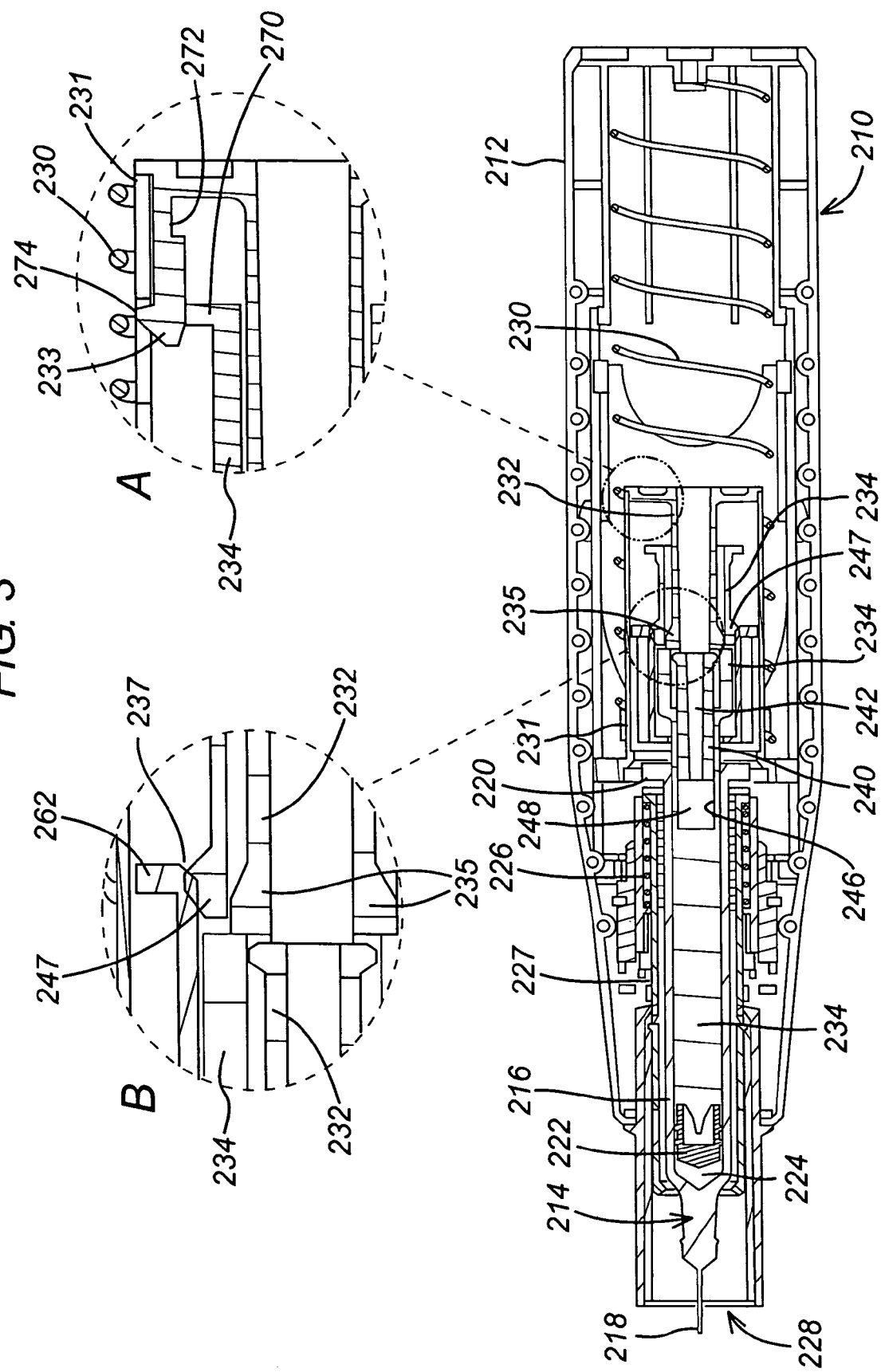
FIG. 3 is likewise a third.
Figure 4:
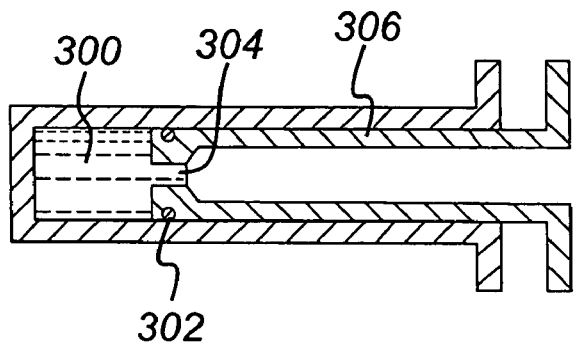
FIG. 4 is a schematic view of a liquid filled damper in accordance with the present invention.

FIG. 3 shows another injection device 210 in which a housing 212 contains a hypodermic syringe 214. The syringe 214 is again of conventional type, including a syringe body 216 terminating at one end in a hypodermic needle 218 and at the other in a flange 220, and a rubber bung 222 that constraints a drug 224 to be administered within the syringe body 216. The conventional plunger that would normally be connected to the bung 222 and used to discharge the contents of the syringe 214 manually, has been removed and replaced with a multi-component drive element as will be described below. Whilst the syringe illustrated is again of hypodermic type, this need not necessarily be so. As illustrated, the housing includes a return spring 226 that biases the syringe 214 from an extended position in which the needle 218 extends from aperture 228 in the housing 212, to a retracted position in which the hypodermic needle 218 is contained within the housing 212. The return spring 226 acts on the syringe 214 via a sleeve 227.

At the other end of the housing is a compression drive spring 230. Drive from the drive spring 230 this transmitted via the multi-component drive to the syringe 214 to advance it from its retracted position to its extended position and discharge its contents through the needle 218. The drive accomplishes this task by acting directly on the drug 224 and the syringe 214. Hydrostatic forces acting through the drug 224 and, to a lesser extent, static friction between the bung 222 and the syringe body 216 initially ensure that they advance together, until the return spring 226 bottoms out or the syringe body 216 meets some other obstruction that retards its motion.

The multi component drive between the drive spring 230 and the syringe 214 again consists of three principal components. The drive sleeve 231 takes drive from the drive spring 230 and transmits it to flexible latch arms 233 on a first drive element 232. These elements are shown in detail "A". The first drive element 232 in turn transmits drive via flexible latch arms 235 to a second drive element 234. These elements are shown in detail "B". As before, the first drive element 232 includes a hollow stem 240, the inner cavity of which forms a collection chamber 242. The second drive element 234 includes a blind for 246 that is open at one end to receive the stem 240 and closed at the other. As can be seen, the bore 246 and the stem 240 define a fluid reservoir 248, within which a highly viscous fluid is contained.

A trigger (not shown) is provided in the middle of the housing 212. The trigger, one operated, serves to decouple the drive sleeve 231 from the housing 212 allowing it to move relative to the housing 212 under the influence of the drive spring 230. The operation of the device is then as follows.

Initially, the drive spring 230 moves the drive sleeve 231, the drive sleeve 231 moves the first drive element 232 and the first drive element 232 moves the second drive element 234, in each case by acting through the flexible matching arms 233, 235. The second drive element 234 moves and, by virtue of static friction and hydrostatic forces acting through the drug 224 to be administered, moves the syringe body 216 against the action of the return spring 226. The return spring 226 compresses and the hypodermic needle 218 emerges from the exit aperture 228 of the housing 212. This continues until the return spring 226 bottoms out or the syringe body 216 meets some other obstruction that retards its motion. Because the static friction between the bung 222 and the syringe body 216 and the hydrostatic forces acting through the drug 224 to be administered are not sufficient to resist the full drive force developed by the drive spring 230, at this point the second drive element 234 begins to move within the syringe body 216 and the drug 224 begins to be discharged. Dynamic friction between the bung 222 and the syringe body 216 and hydrostatic forces acting through the drug 224 to be administered are, however, sufficient to retain the return spring 226 in its compressed state, so the hypodermic needle 218 remains extended.

Before the second drive element 234 reaches the end of its travel within the syringe body 216, so before the contents of the syringe have fully discharged, the flexible latch arms 235 linking the first and second drive elements 232, 234 reach a constriction 237. The constriction 237 is formed by a component 262 that is initially free to move relative to all other components, but that is constrained between the syringe flange 220 and additional flexible arms 247 on the second drive element 234. These additional flexible arms 247 overlie the flexible arms 235 on the first drive element 232, by means of which drive is transmitted to the second drive element 234. FIG. 3 illustrates the injection device 210 at the position where the additional flexible arms 247 are just making contact with the constriction 237 in the component 262.

The constriction 237 moves the additional flexible arms 247 inwards, aided by the bevelled surfaces on both, and the additional flexible arms 247 in turn move the flexible arms 235, by means of which drive is transmitted from the first drive element 232 to the second drive element 234, inwards from the position shown to a position at which they no longer couple the first and second drive elements together. Once this happens, the first drive element 232 acts no longer on the second drive element 234, allowing the first drive element 232 to move relative to the second drive element 234.

Because the highly viscous fluid is contained within a reservoir 248 defined between the end of the first drive element 232 and the blind bore 246 in the second drive element 234, the volume of the reservoir 248 will tend to decrease as the first drive element 232 moves relative to the second drive element 234 when the former is acted upon by the drive spring 230. As the reservoir 248 collapses, highly viscous fluid is forced into the collection chamber 242. Thus, once the flexible latch arms 235 have been released, the force exerted by the drive spring 230 does work on the highly viscous fluid, causing it to flow into the collection chamber 242, and also acts hydrostatically through the fluid and through friction between the first and second drive elements 232, 234, thence via the second drive element 234. Losses associated with the flow of the highly viscous fluid do not attenuate the force acting on the body of the syringe to a great extent. Thus, the return spring 226 remains compressed and the hypodermic needle remains extended.

After a time, the second drive element 234 completes its travel within the syringe body 216 and can go no further. At this point, the contents of the syringe 214 are completely discharged and the force exerted by the drive spring 230 acts to retain the second drive element 234 in its terminal position and to continue to cause the highly viscous fluid to flow into the collection chamber 142, allowing the first drive element 232 to continue its movement.

A flange 270 on the rear of the second drive element 234 normally retains the flexible arms 233 in engagement with the drive sleeve 231. However, before the reservoir 248 of highly viscous fluid is exhausted, the flexible latch arms 233 linking the drive sleeve 231 with the first drive element 232 move sufficiently far forward relative to the second drive element 234 that the flange 270 is brought to register with a rebate 272 in the flexible arms 233, whereupon it ceases to be effective in retaining the flexible arms 233 in engagement with the drive sleeve 231. Now, the drive sleeve 231 moves the flexible latch arms 233 inwards from the position shown to a position at which they no longer couple the drive sleeve 231 to the first drive element 232, aided by the bevelled latching surfaces 274 on the flexible arms 233. Once this happens, the drive sleeve 231 acts no longer on the first drive element 232, allowing them to move relative to each other. At this point, of course, the syringe 214 is released, because the forces developed by the drive spring 230 are no longer being transmitted to the syringe 214, and the only force acting on the syringe will be the return force from the return spring 226. Thus, the syringe 214 now returns to its retracted position and the injection cycle is complete.

In the injection devices described, and in any injection device according to the invention, the highly viscous fluid may be any fluid that has the appropriate properties. Silicone oil and silicone grease are examples of fluids that may be selected to have a kinematic viscosity at 20° C. of 12500 centistokes or more. Moreover, both are excellent lubricators and certainly silicone grease is sufficiently resistant to flow that it will not accidentally discharge from the open end of the collection chamber. Furthermore, the reservoir in the second drive element is simple to fill before stem of the first drive element is pushed into place. The volume of fluid need not be accurately controlled, since excess fluid will be expelled into the collection chamber. The fluid will then fills the vent and prevents the ingress of dirt or other contaminants that could lead to blockage.

Although preferred damping mechanisms using a highly viscous fluid have been described, it will of course be understood that other damping mechanisms that use a highly viscous fluid are possible. Thus, the highly viscous fluid may be used to damp the movement of components of the device other than elements that transmit drive from the drive actuator to the syringe. Many of the advantages associated with the use of a highly viscous fluid are independent of the other details of the damping mechanism.

A functional upper limit on the dynamic viscosity of the highly viscous fluid is set by the need for it to act as an effective damper. In practical embodiments of this invention, including the embodiments just described, it is unlikely that dynamic viscosities in excess of 150,000 centiPoise would be effective. Even fluids with dynamic viscosities in excess of 60,000 centiPoise would appear to have limited applicability.

ANNEX

Measurement of Dynamic Viscosity

1. Introduction

A liquid filled damper has been proposed for use in the device. The damper consists of a small bore filled with fluid and a hollow piston with a small hole in the centre. When a force is applied the fluid is forced through the hole and into the centre of the piston.

This document describes a test method by which the dynamic viscosity of the fluid may be determined.

2. Description of Damper
3. Theoretical Treatment of Flow Through Bleed Hole
3.1 Derivation The following analysis is applied to laminar flow of fluid in an axisymmetric pipe, in this case the bleed hole in the piston.

Resolving forces on a cylindrical element:

$$2\pi L\tau = \Delta PA \quad \text{(i)}$$

$$A = \pi r^2$$

$$\therefore \tau = \frac{\Delta P}{L}\frac{r}{2}$$

Assuming the fluid is Newtonian and referencing flow from the centreline:

$$\tau = -\mu\frac{du}{dr} \quad \text{(ii)}$$

Equating (i) and (ii):

$$\frac{-\Delta P}{2\,\mu L}r = \frac{du}{dr}$$

Integrating:

$$u = \frac{-\Delta P r^2}{4\,\mu L} + C_1$$

Boundary conditions:
u=0 at r=R
u=max at r=0

$$\therefore C_1 = \frac{\Delta P}{L}\frac{R^2}{4\,\mu} \quad \text{(iii)}$$

$$\therefore u = \frac{\Delta P}{4\,\mu L}(R^2 - r^2)$$

Examining an annular element:

δQ=uδA  Elemental volumetric flow rate

δA≈2πrδr $$\therefore \delta Q = \frac{\Delta P \pi r}{2\,\mu L}(R^2 - r^2)\delta r$$

Integrating between r=0 and r=R:

$$Q = \frac{\Delta P\pi}{2\,\mu L}\int_O^R r(R^2 - r^2)\delta \quad \text{Volumetric flow rate}$$

$$Q = \frac{\Delta P\pi R^4}{8\,\mu L}$$

$$Q = \frac{\Delta P\pi d^4}{128\,\mu L}$$

For the case of the damper, neglecting friction in the piston, mass of the piston and assuming a perfect seal between piston and bore:

$$Q = \frac{\Delta P\pi d^4}{128\,\mu L} \quad \text{(iv)}$$

Volumetric flow rate through bleed hole $$\Delta P = \frac{4F}{\pi(d_2^2 - d_1^2)}$$

(v)
Pressure from piston above atmospheric pressure $$Q = A_{piston} v_{piston}$$

$$\therefore v_{piston} = \frac{4Q}{\pi(d_2^2 - d_1^2)}$$

$$v_{piston} = \frac{\Delta P d}{32 \,\mu L(d_2^2 - d_1^2)}$$

$$v_{piston} = \frac{F d_1^4}{8\pi \,\mu L(d_2^4 + d_1^4 - 2d_1^2 d_2^2)}$$

$$\frac{1}{v_{piston}} = \frac{8\pi \,\mu L(d_2^4 + d_1^4 - 2d_1^2 d_2^2)}{F d_1^4}$$

Figure 5:
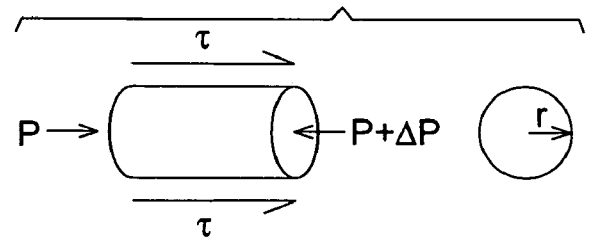
FIG. 5 is a schematic view of a test apparatus in accordance with the present invention.
Figure 6:
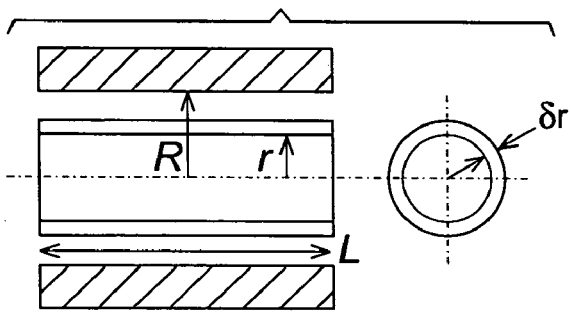
FIG. 6 is a schematic view of a test apparatus in accordance with the present invention.
Figure 7:
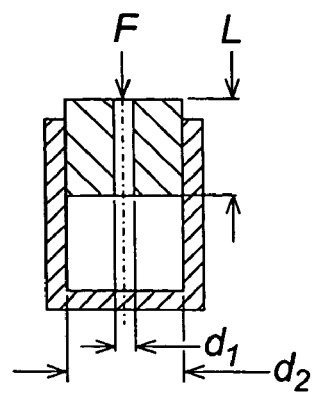
FIG. 7 is a schematic view of a test apparatus in accordance with the present invention.
Figure 8:
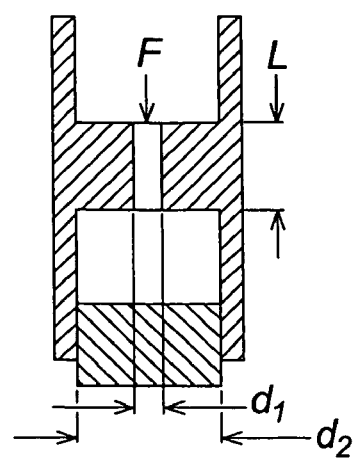
FIG. 8 is a schematic view of a test apparatus in accordance with the present invention.

Volumetric flow rate equal to rate at which piston displaces fluid (vi)
Substituting (iv) for Q
Substituting (v) for P
Time delay per unit of piston travel
4. Apparatus and Method The test apparatus shall consist of two rigid, rotationally symmetrical, coaxial bodies as are illustrated schematically in FIG. 5. One contains a cylindrical bore having an internal diameter in the range 4.45 to 4.55 mm. Let this diameter be $d_2$. It also includes a coaxial, circular bleed hole having a diameter in the range 0.65 to 0.75 mm. Let this diameter be $d_1$. The length of the bleed hole is in the range 1.95 to 2.05 mm. Let this length be L. The bleed hole leads to a collection chamber, also of diameter $d_2$.

The second coaxial body has a hollow cylindrical piston that forms a sufficiently good seal with the bore in the other body that there is no significant loss of fluid between the cylindrical surfaces of the bodies during the course of the test. Any force necessary to overcome dynamic friction between the cylindrical surfaces of the bodies can be measured in the presence of an amount of test fluid sufficient to lubricate the interface.

With the bleed hole temporarily stopped, the first coaxial body is inverted and a sample of the fluid to be tested is introduced into the cylindrical bore to a depth of at least 6 mm. The second coaxial body is then inserted into the first. The apparatus is then righted and the bleed hole unstopped. The second coaxial body is held stationary and the first is lowered until the fluid emerges from the bleed hole, where it is collected. There must be at least 5 mm of travel remaining at this stage.

A downward force is applied to the first coaxial body causing it to move. The size of this force is such that the net force acting on the surface of the fluid, which is the applied force, less the force necessary to overcome dynamic friction between the cylindrical surfaces of the bodies, plus the weight of the first coaxial body, is in the range 9.95 to 10.05 N. Let this net force be F.

A position transducer is attached to the second coaxial body and to a data logger, by means of which a plot of position vs. time is obtained. Once the second coaxial body has moved by at least 1.5 mm in response to the applied force, the time taken for it to move by a further 2.0 mm is measured from the position vs. time plot. At least 1.5 mm of travel must remain after this 2 mm interval. This time measured is divided by two to yield an average time to travel 1.0 mm. Let this time be $t_1$.

According to the analysis presented above, if $v_{piston}$ is measured in SI units, $$\frac{1}{v_{piston}} = 1000 t_1 = \frac{8\pi \,\mu L(d_2^4 + d_1^4 - 2d_1^2 d_2^2)}{F d_1^4}$$

Or, in other words, $$\mu = \frac{125 t_1 F d_1^4}{\pi L(d_2^4 + d_1^4 - 2d_1^2 d_2^2)}$$

Thus is the dynamic viscosity determined.

The test procedure is to be repeated another four times with different samples of the fluid and the mean of the five results obtained is taken as the dynamic viscosity of the fluid.

This procedure is applicable to both Newtonian and non-Newtonian fluids. Especially in the case of fluids that depart considerably from Newtonian behaviour, the various dimensions of the apparatus and the applied force should be exactly at the mid-point of the ranges given above.

The invention claimed is:

1. An injection device comprising:
   a housing adapted to receive a syringe having a discharge nozzle, the housing including means for biasing the syringe from an extended position in which the discharge nozzle extends from the housing to a retracted position in which the discharge nozzle is contained within the housing;
   an actuator;
   a drive acted upon by the actuator and in turn acting on the syringe to discharge its contents through the discharge nozzle;
   a decoupling mechanism, activated when the drive has been advanced to a nominal decoupling position, to decouple a first component of the device from acting on a second component and allow the first component to move relative to a second;
   a release mechanism, activated when the said first component has reached a nominal release position relative to the second, to release the syringe from the action of the actuator, whereupon the biasing means restores the syringe to its refracted position; and
   a highly viscous fluid damping the movement of the said first component relative to the second, so that the release of the syringe is delayed after the activation of the decoupling mechanism to allow the remaining contents of the syringe to be discharged before the syringe is released.

2. An injection device according to claim 1 in which the first and second components of the device are first and second elements of the drive, of which the first is acted upon by the actuator and the second acts upon the syringe to advance it from its retracted position to its extended position and discharge its contents through the discharge nozzle, the first drive element being capable of movement relative to the second when the former is acted upon by the actuator and the latter is restrained by the syringe.

3. An injection device according to claim 2 further comprising a reservoir defined in part by the first drive element and in part by the second drive element, the volume of the reservoir tending to decrease as the first drive element moves relative to the second when acted upon by the actuator, the reservoir containing the highly viscous fluid and having a vent through which the fluid escapes as the volume of the reservoir decreases.

4. An injection device comprising:
- a housing adapted to receive a syringe having a discharge nozzle, the housing including means for biasing the syringe from an extended position in which the discharge nozzle extends from the housing to a retracted position in which the discharge nozzle is contained within the housing;
- an actuator;
- first and second drive elements, of which the first is acted upon by the actuator and the second acts upon the syringe to advance it from its retracted position to its extended position and discharge its contents through the discharge nozzle, the first drive element being capable of movement relative to the second when the former is acted upon by the actuator and the latter is restrained by the syringe;
- a reservoir defined in part by the first drive element and in part by the second drive element, the volume of the reservoir tending to decrease as the first drive element moves relative to the second when acted upon by the actuator, the reservoir containing a highly viscous fluid and having a vent through which the fluid escapes as the volume of the reservoir decreases;
- a release mechanism, activated when the first drive element has been advanced to a nominal release position, and adapted to release the syringe from the action of the actuator, whereupon the biasing means restores the syringe to its retracted position; and
- a coupling that prevents the first drive element from moving relative to the second until they have been advanced to a nominal decoupling position that is less advanced than the said nominal release position.

5. An injection device according to claim 4 in which the coupling comprises a decoupling mechanism, activated when the drive elements have been advanced to the said nominal decoupling position.

6. An injection device according to any one of claims 4 in which:
- the coupling is a third drive element acting upon the first and second drive elements;
- the decoupling mechanism is adapted to decouple the third drive element from the second so that the third drive element acts only it no longer once the said nominal decoupling position has been reached, thus allowing the first drive element to move relative to the second; and
- the release mechanism is adapted to decouple the third drive element from the first so that the third drive element acts upon it no longer once the said nominal release position has been reached, thus releasing the syringe from the action of the actuator.

7. An injection device according to any one of claims 4 in which:
- the coupling comprises cooperating features of the first and second drive elements allowing the first to act upon the second;
- the decoupling mechanism is adapted to decouple the first drive element from the second so that the first drive element acts no longer on the second once the said nominal decoupling position has been reached, thus allowing the first drive element to move relative to the second; and
- the release mechanism is adapted to decouple the first drive element from the actuator so that the actuator acts upon it no longer once the said nominal release position has been reached, thus releasing the syringe from the action of the actuator.

8. An injection device according to any one of claims 4 in which the vent is in communication with a collection chamber defined by one drive element, within which the escaped fluid is collected.

9. An injection device according to any one of claims 4 in which one drive element includes a stem and the other includes a bore that is open at one end to receive the stem, the bore and the stem thus defining the fluid reservoir.

10. An injection device according to claim 4 in which one drive element includes a stem and defines the vent and the collection chamber and the other drive element includes a blind bore that is open at one end to receive the stem and closed at the other, the bore and the stem thus defining the fluid reservoir.

11. An injection device according to claim 4 or claim 4 in which the collection chamber is defined by a bore in the said one element, being open at one end and closed at the other but for the vent.

12. An injection device according to any one of claims 4 in which the said one drive element is the first drive element.

* * * * *